US008672961B2

(12) United States Patent
Haas et al.

(10) Patent No.: US 8,672,961 B2
(45) Date of Patent: Mar. 18, 2014

(54) SURGICAL SEVERING INSTRUMENT

(75) Inventors: Alexander Haas, Donaueschingen (DE); Natalia Peters, Blumberg (DE)

(73) Assignee: Aesculap AG, Tuttlingen (DE)

( * ) Notice: Subject to any disclaimer, the term of this patent is extended or adjusted under 35 U.S.C. 154(b) by 595 days.

(21) Appl. No.: 12/657,165

(22) Filed: Jan. 14, 2010

(65) Prior Publication Data

US 2010/0198245 A1    Aug. 5, 2010

(30) Foreign Application Priority Data

Feb. 4, 2009   (DE) .......................... 10 2009 007 455

(51) Int. Cl.
  *A61B 17/32* (2006.01)
(52) U.S. Cl.
  USPC ........................................................ 606/174
(58) Field of Classification Search
  USPC ................. 606/120, 206, 119, 118, 174, 207; 30/92, 96, 134; 81/305–307, 311, 312, 81/418
  See application file for complete search history.

(56) References Cited

U.S. PATENT DOCUMENTS

| | | | | |
|---|---|---|---|---|
| 3,166,071 A | * | 1/1965 | Mayer | ........................... 606/120 |
| 4,026,294 A | * | 5/1977 | Mattler | ........................ 606/120 |
| 4,428,374 A | * | 1/1984 | Auburn | ......................... 606/174 |
| 4,572,181 A | * | 2/1986 | Mattler | ......................... 606/174 |
| 4,600,007 A | * | 7/1986 | Lahodny et al. | .............. 606/174 |
| 4,644,953 A | * | 2/1987 | Lahodny et al. | .............. 606/174 |
| 5,611,146 A | * | 3/1997 | Ducret | ............................. 30/92 |
| 5,822,865 A | | 10/1998 | Bosch et al. | |
| 5,925,052 A | * | 7/1999 | Simmons | ...................... 606/120 |
| 6,358,268 B1 | | 3/2002 | Hunt et al. | |
| 6,780,195 B2 | * | 8/2004 | Porat | ............................. 606/120 |
| 2008/0015566 A1 | | 1/2008 | Livneh | |
| 2009/0112246 A1 | * | 4/2009 | Weisshaupt et al. | .......... 606/174 |

FOREIGN PATENT DOCUMENTS

DE          195 34 831        3/1997

* cited by examiner

*Primary Examiner* — S. Thomas Hughes
*Assistant Examiner* — Julie A Szpira
(74) *Attorney, Agent, or Firm* — Lipsitz & McAllister, LLC

(57) ABSTRACT

In a surgical severing instrument comprising two cutting jaws movable relative to each other from an open position to a cutting position by means of hand grips movable relative to each other, in order to improve the handling, in particular, of the severed parts, it is proposed that two clamping jaws movable relative to each other from an initial position to a clamping position be arranged alongside the cutting jaws, and that actuators be provided on the surgical severing instrument, which, upon movement of the cutting jaws from the open position to the cutting position, simultaneously move the clamping jaws from their initial position to the clamping position.

13 Claims, 8 Drawing Sheets

FIG. 7

SURGICAL SEVERING INSTRUMENT

The present disclosure relates to the subject matter disclosed in German application number 10 2009 007 455.4 of Feb. 4, 2009, which is incorporated herein by reference in its entirety and for all purposes.

BACKGROUND OF THE INVENTION

The invention relates to a surgical severing instrument having two cutting jaws movable relative to each other from an open position to a cutting position by means of hand grips which are movable relative to each other.

Such severing instruments are often of pliers-like construction and serve to sever tissue or parts of implants, for example, for severing protruding wire pins or the like. The cutting jaws may be normal cutting arms of scissors-like construction or in the fashion of cutting pliers. In all cases, the cutting jaws are moved towards each other with opposed cutting edges and can thereby sever material that is arranged between them.

In particular, when severing parts of implants, it is necessary to collect the severed parts carefully and remove them from the body when the operation takes place inside the body.

A pliers-like cutting element of this kind is described, for example, in DE 195 34 831 C2.

Surgical severing instruments are also known, which are combined with clamping jaws, the function of the clamping jaws consisting, for example, in grasping tissue or objects which are to be severed. In known instruments of this kind, separate actuating members are provided for actuating the clamping jaws and for actuating the cutting jaws. The actuating members are actuated separately using the hand grip, so that the surgeon can carry out a clamping and a cutting procedure successively (U.S. Pat. No. 6,358,268 B1; U.S. Pat. No. 4,600,007). This is awkward and may also result in cutting procedures being carried out without the cut-off parts being secured by the clamping jaws.

The object of the invention is to so construct a generic surgical severing instrument that the handling while collecting severed parts can be improved with it.

SUMMARY OF THE INVENTION

This object is accomplished, in accordance with the invention, in a surgical instrument of the kind described at the outset by two clamping jaws movable relative to each other from an initial position to a clamping position being arranged alongside the cutting jaws, and by actuators being provided on the surgical severing instrument, which, upon movement of the cutting jaws from the open position to the cutting position, simultaneously move the clamping jaws from their initial position to the clamping position.

Accordingly, upon actuating the cutting jaws, the clamping jaws are also closed as a consequence thereof, i.e., moved to the clamping position, so that it is ensured that during the severing or cutting by means of the cutting jaws, the severed parts are definitely grasped by the clamping jaws without the user having to specially actuate the clamping jaws using separate handling members. By providing actuators on the severing instrument, actuation of the clamping jaws is bound to occur for each cutting procedure.

In particular, it may be provided that the cutting jaws and/or the clamping jaws are movable relative to each other by being pivoted about a pivot axis. The cutting jaws and the clamping jaws are preferably mounted coaxially.

It is particularly advantageous for the clamping jaws to be each connected to an actuating lever, and for the clamping jaws to be moved from the initial position to the clamping position by the actuating levers being brought closer together. This results in a pliers-type instrument.

It is expedient for the actuators to be arranged on the hand grips of the severing instrument and to engage the actuating levers of the clamping jaws.

In particular, it may be provided that the actuators are projections on the hand grips, which abut on the outer sides of the actuating levers.

In accordance with a particularly preferred embodiment, it is provided that a spring element which attempts to move the cutting jaws or the clamping jaws to their open position or initial position engages the severing instrument and/or the clamping jaws. Accordingly, the severing instrument is transferred to the cutting position against the action of these spring elements, and, similarly, the clamping jaws are transferred to their clamping position against the action of the spring element. Prior to the actuation, both the cutting jaws and the clamping jaws are therefore open, i.e., they are located in the open position or in the initial position.

In accordance with a further preferred embodiment, a locking device for enabling movement of the clamping jaws from the initial position to the end position, but not in the reverse direction, is associated with the clamping jaws. The clamping jaws thus remain in the clamping position after being moved into it, and they therefore retain between them parts clamped between the clamping jaws and severed after the cutting procedure. The cutting jaws can be moved back into the open position again after a cutting procedure, but the clamping jaws remain in the closed clamping position also after completion of the cutting procedure and after opening of the severing instrument.

For example, the locking device may be constructed as a latching bar which is operative between the actuating levers of the clamping jaws, as is known per se in pliers-type surgical instruments.

In another preferred embodiment, it is provided that the locking device is formed by latching surfaces on the clamping jaws, which are arranged concentrically with a pivot axis of the clamping jaws and abut on each other. In particular, these latching surfaces may be fitted with saw-tooth-shaped teeth, which allow the latching surfaces to slide past each other in one direction, but not in the reverse direction.

It is particularly advantageous for the clamping jaws and possibly the actuating levers to be constructed as a structural unit which is detachably connectable to the severing instrument. Firstly, it is thus possible, after detachment of this structural unit from the severing instrument, to use the severing instrument without this structural unit, i.e., in the usual manner as a simple severing instrument without any additional clamping device, and, secondly, it is possible to fit a severing instrument with a structural unit which brings about the clamping of the severed components, and to construct this structural unit as a disposable part, for example, as a plastic part, in which case, the severing instrument is fitted with a new structural clamping unit for each operation.

In particular, the structural unit may be in the form of pliers having two arms pivotably connected to each other, which form actuating levers and carry the clamping jaws at their distal ends. This pliers-like structural unit may possibly have a significantly shorter length than the severing instrument, it sufficing for the actuating levers of the structural clamping unit to extend over part of the length of the hand grips of the severing instrument.

In accordance with a preferred further development of the severing instrument, it may also be provided that the cutting jaws carry deforming projections which, when the components arranged between the cutting jaws are being severed, bend locking elements arranged on the components or on elements carried by the components and thereby lock the locking elements relative to other components or elements. Such a severing instrument not only holds the severed components securely by means of the closed clamping jaws but also locks the parts remaining, for example, on an implant relative to one another by deforming or bending locking elements provided thereon by means of the deforming projections arranged on the cutting jaws. The cutting jaws are therefore given a double function, namely the function of severing implant parts or the like, on the one hand, and the function of deforming or bending parts in order to lock them, on the other hand.

The following description of preferred embodiments of the invention serves in conjunction with the drawings for further explanation.

DETAILED DESCRIPTION OF THE INVENTION

The drawings show a pliers-type severing instrument 1 with two cutting jaws 2, 3 which are mounted for pivotal movement relative to each other. The cutting jaws 2, 3 are engaged by an arm 4 and 5, respectively. The arms 4, 5 are also pivotably connected to each other and also pivotably connected to the cutting jaws 2 and 3, respectively, so that upon pivotal movement of the two arms 4, 5 relative to each other, the two cutting jaws 2, 3 are also pivoted relative to each other about their common pivot bearing.

The two cutting jaws 2, 3 are pressed apart by leaf-shaped spring elements 6, 7 arranged between the two arms 4, 5, so that upon pressing together the two arms 4, 5, the arms 4, 5 have to be pressed together against the force of these spring elements 6, 7. Accordingly, the arms 4, 5 are normally in the open position in which they are maximally spaced from each other, and, as a result, the cutting jaws 2, 3 are also in an open position in which cutting edges 8, 9 on the cutting jaws 2, 3 are maximally spaced from each other. Such a severing instrument 1 in the form of cutting pliers is known per se and can be used for severing portions of tissue or implant parts or the like. In the embodiment shown in the drawings, this severing instrument 1 is used to sever and thereby shorten metallic pins 10, 11 which extend through an intervertebral implant 12, after implantation into the intervertebral space between two adjacent vertebral bodies 13, 14. Of the intervertebral implant 12 shown in the drawings, it is essentially the pins 10, 11 that are of importance, and, therefore, the further construction of the intervertebral implant 12 will not be explained in greater detail.

After insertion of the intervertebral implant 12, the pins 10, 11 protrude from it and must be shortened. This is done with the severing instrument 1.

The severing procedure is carried out close to an end plate 15 of the intervertebral implant 12, through which the two pins 10, 11 pass. For the severing of the pins, this end plate 15 is placed in a recess 16, 17 of the two cutting jaws 2, 3, which is located immediately beside the cutting edges 8, 9 of the cutting jaws 2, 3 (FIG. 5), so that an exact positioning of the intervertebral implant 12 and the pins 10, 11 protruding from it relative to the cutting jaws 2, 3 is thereby enabled.

Arranged on the severing instrument 1 on the side of the cutting jaws 2, 3 located opposite these recesses 16, 17 is a clamping instrument 18, also of pliers-type construction, which has two clamping jaws 19, 20 pivotably connected to each other, which are fixedly connected to an arm-like actuating lever 21 and 22, respectively. The actuating levers, each carrying a clamping jaw, are pivotably connected to each other by a bearing shaft 23 extending transversely through them. They intersect at the bearing point, so that the clamping jaws 19, 20 can be pivoted out of an open initial position into a closed clamping position when the two actuating levers 21, 22 are pivoted relative to each other. There is also provided between the actuating levers 21, 22 an elastic spring element 24, which pivots the actuating levers 21, 22 into the open position and which has to be deformed when the actuating levers 21, 22 are pivoted relative to each other.

This pliers-type clamping instrument 18 is arranged at the side of the severing instrument 1 in such a way that the pivot axis of the clamping jaws 19, 20 defined by the bearing shaft 23 and the pivot axis of the two cutting jaws 2, 3 are arranged coaxially, so that in the closed state the cutting edges 8, 9 of the cutting jaws 2, 3 and the clamping surfaces of the clamping jaws 19, 20 are located in a common plane.

Arranged on the two arms 4, 5 are side pins 25, 26, which engage the outer sides of the two actuating levers 21, 22, which have depressions 27, 28 for receiving the pins 25, 26. The clamping instrument 18 may be held on the severing instrument 1 for detachment in its entirety therefrom, for example, by the bearing shaft 23 being screwed into the severing instrument 1, preferably into a bearing shaft, not shown in the drawings, of the cutting jaws 2, 3. By releasing this screw connection, the connection of the clamping instrument 18 to the severing instrument 1 can also be thereby released, i.e., it is readily possible to exchange the clamping instrument 18 in a simple way. This clamping instrument can therefore be designed as a disposable part. For example, this clamping instrument could consist of a sterilizable plastic material, which after completion of an operation is detached from the severing instrument 1 and then disposed of.

Mounted for pivotal movement on one of the two actuating levers of the clamping instrument 18 is a latching bar 29, which passes through an opening 30 on the other actuating lever 22 and carries saw-tooth-shaped projections 31 on one side thereof. These interact with a corresponding projection, not shown in the drawings, in the opening 30 in such a way that the projections 31 slide along this projection in the opening 30 when the two actuating levers 21, 22 are pivoted relative to each other, but that the projections 31 so engage the projection in the opening 30 that an opening of the actuating levers 21, 22, i.e., a pivoting apart, is prevented. To pivot the two actuating levers 21, 22 apart, the latching bar 29 must be pivoted by pressure on its free end constructed as a grip surface 32. The latching bar 29 is then pressed by a spring element 33 with its projections 31 against the projection in the opening 30.

This locking device formed by the latching bar 29 thus makes it possible to close the clamping instrument 18. An opening, on the other hand, is only possible when the user intentionally presses the grip surface 32 of the latching bar 29.

The clamping instrument 18 is closed as a consequence of the closing movement of the arms 4, 5, and the parts of the pins 10, 11 severed during the closing of the cutting jaws 2, 3 are held between the clamping jaws 19, 20 which are also closed. When the severing instrument 1 is opened again, the clamping instrument 18 still remains closed owing to the latching bar 29 and continues to hold the cut-off parts of the pins 10, 11 firmly, which can then be removed from the operating site together with the severing instrument 1 and the clamping instrument 18 held thereon. The latching bar 29 is usually only released outside of the operating site, so that the severed parts can then be removed. These may, however, also remain in the closed clamping instrument 18, which is then detached in its entirety from the severing instrument 1 and disposed of.

The clamping instrument 18 thus ensures that the severed parts of the pins 10, 11 cannot get lost in an uncontrolled manner. Moreover, the clamping instrument 18 has the additional advantage that shortly before the severing of the pins 10, 11, these are secured between the clamping jaws 19, 20, so that the pins are prevented from sliding away during the severing procedure.

In the embodiment of FIGS. 1 to 5, the locking device of the actuating levers 21, 22 is formed by the latching bar 29.

Figure 8:
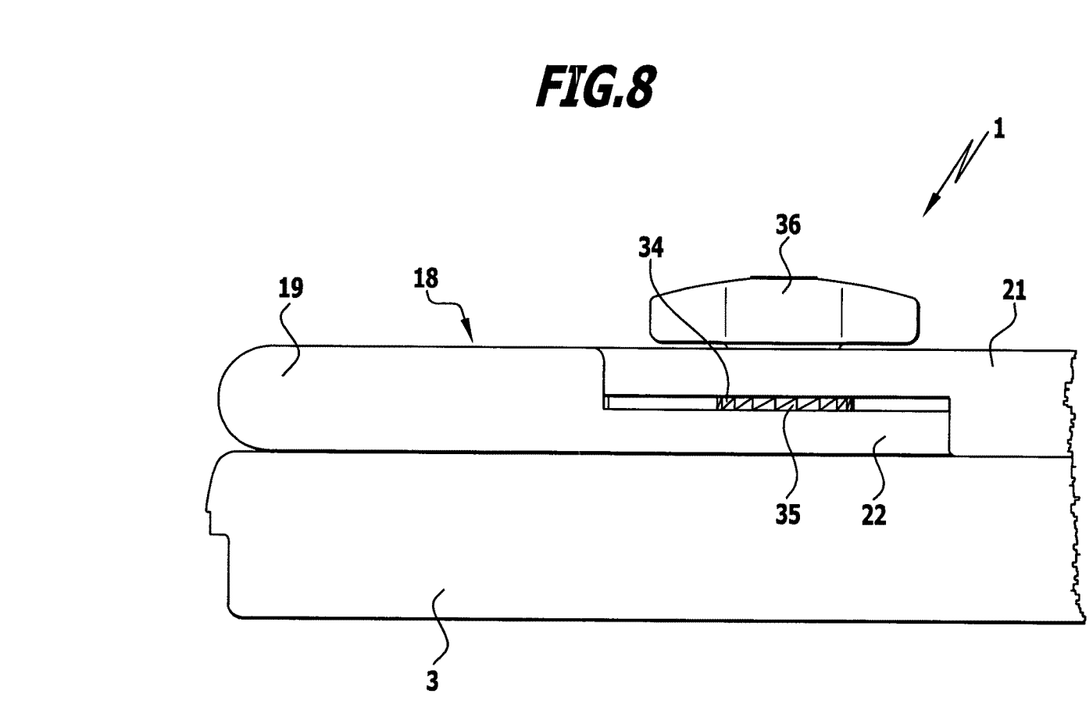
FIG. 8 shows a side view of a modified embodiment of a severing instrument in the area of the cutting jaws and the clamping jaws with a locking device in the form of latching surfaces lying with surface-to-surface contact against one another.

In contrast thereto, in the embodiment according to FIG. 8, which is otherwise of similar construction and in which like parts bear like reference numerals, a free pivotability of the two actuating levers 21, 22 in the closing direction and a blocking or locking in the opening direction are achieved by the two actuating levers 21, 22 respectively carrying on the sides that face each other a latching disc 34, 35 which concentrically surrounds the bearing shaft 23. These two latching discs 34, 35 are fitted with saw-tooth-shaped teeth which engage one another, so that the latching discs 34, 35 can slide past each other in one direction of rotation, whereas a blocking occurs in the opposite direction of rotation. The two latching discs 34, 35 thus form a kind of freewheel by means of which a closed position once reached can also be retained.

This can only be released for the user by the clamping instrument 18 being completely detached from the severing instrument 1, for example, by screwing out the bearing shaft 23 by means of a turning knob 36 which is connected to it.

Figure 1:
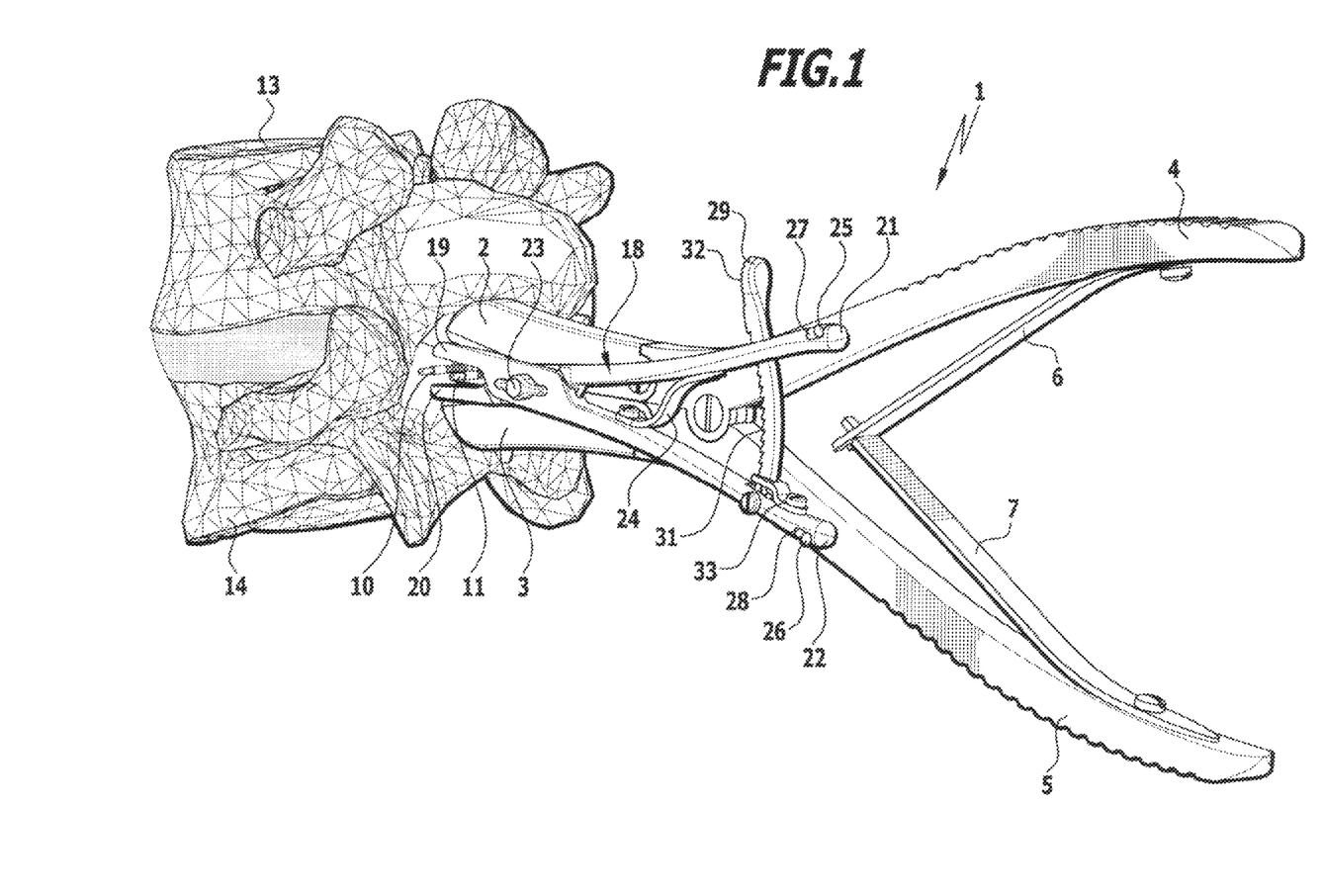
FIG. 1 shows a perspective view of a pliers-type severing instrument with clamping pliers in engagement during the shortening of metal pins on an intervertebral implant.
Figure 2:
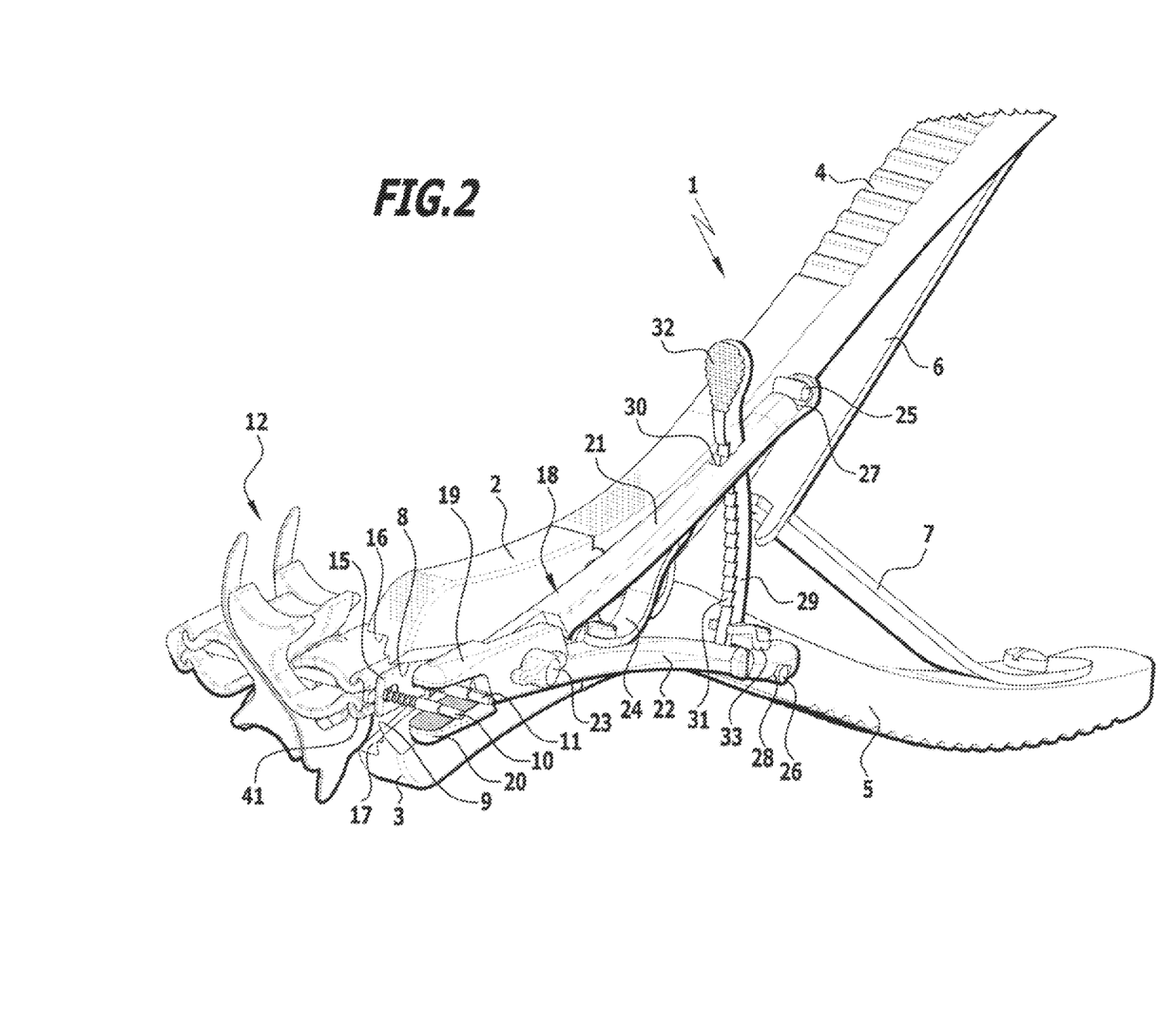
FIG. 2 shows a perspective view of the severing instrument of FIG. 1 with open cutting jaws and open clamping jaws.
Figure 3:
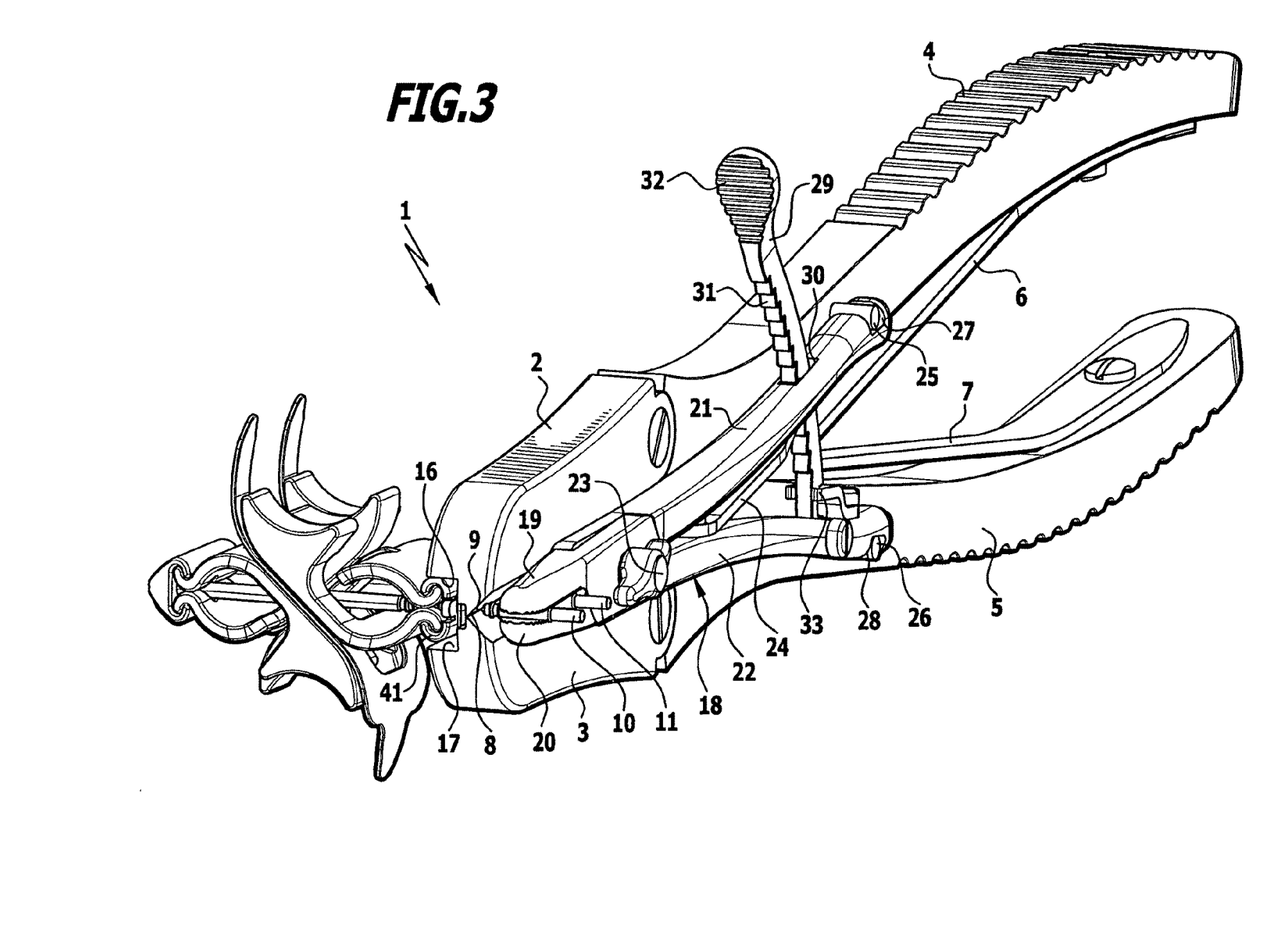
FIG. 3 shows a view similar to FIG. 2 with closed cutting jaws and closed clamping jaws.
Figure 4:
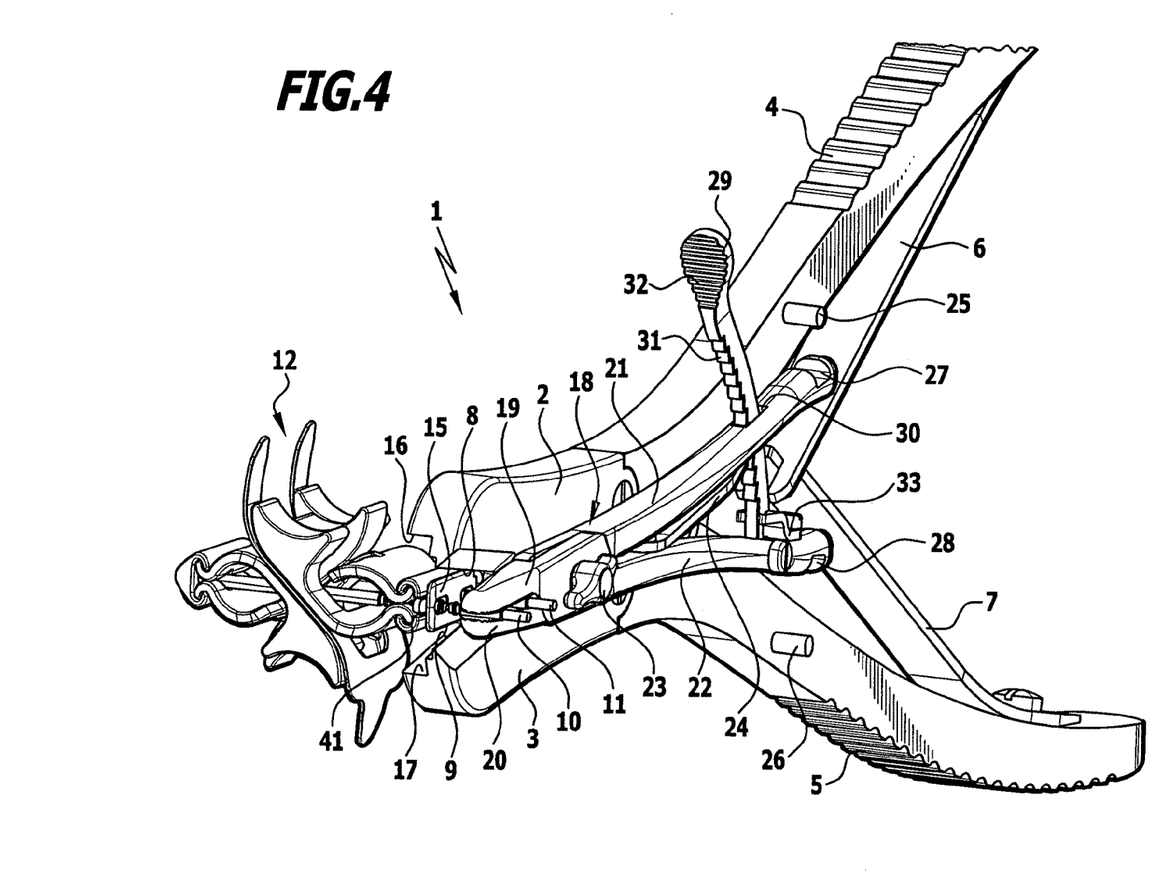
FIG. 4 shows a view similar to FIG. 3 with cutting jaws opened after the cutting procedure and clamping jaws still closed.
Figure 5:
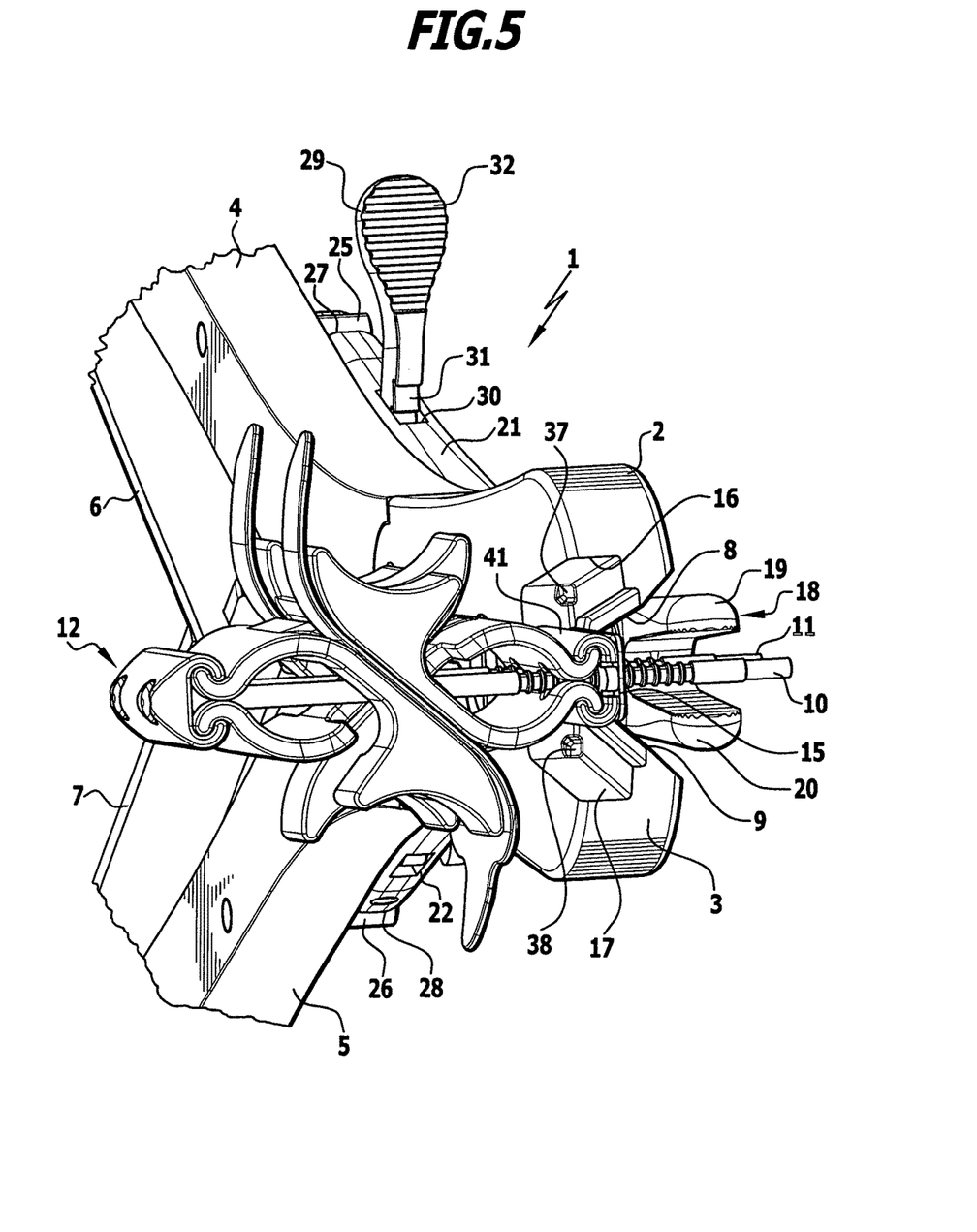
FIG. 5 shows a perspective view of the severing instrument of FIG. 2 in the area of the cutting jaws and the clamping jaws.
Figure 6:
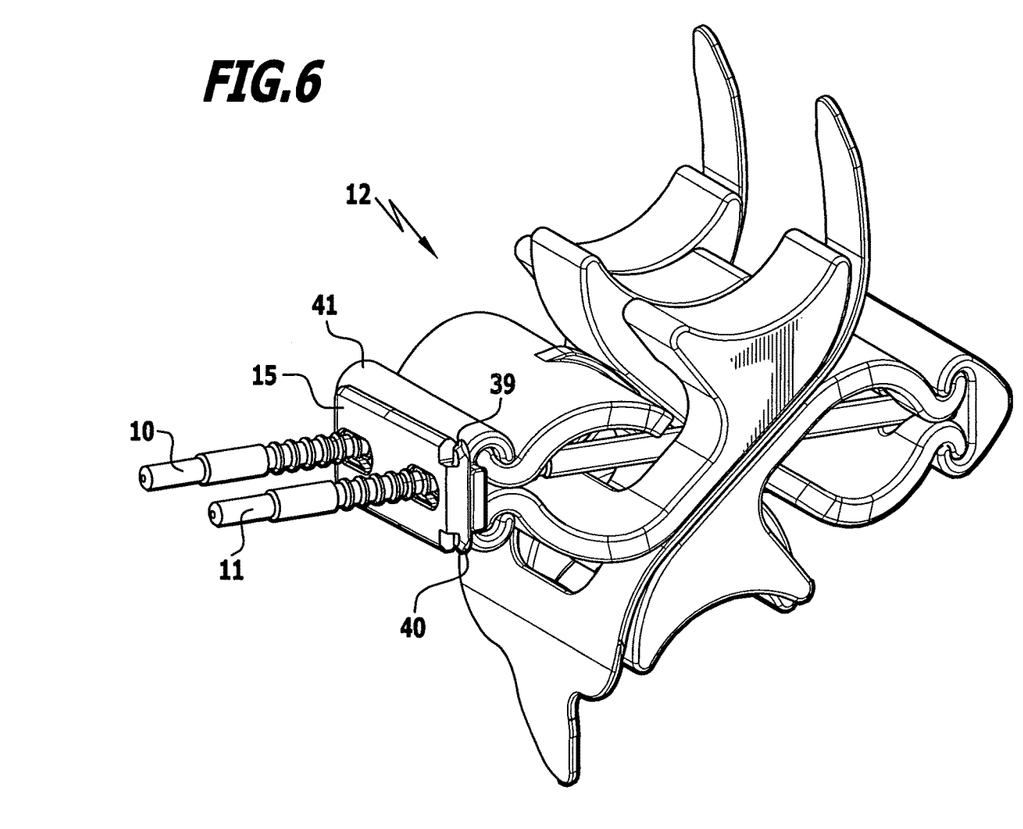
FIG. 6 shows a perspective view of an intervertebral implant with locking elements prior to a cutting procedure and prior to the bending of the locking elements.
Figure 7:
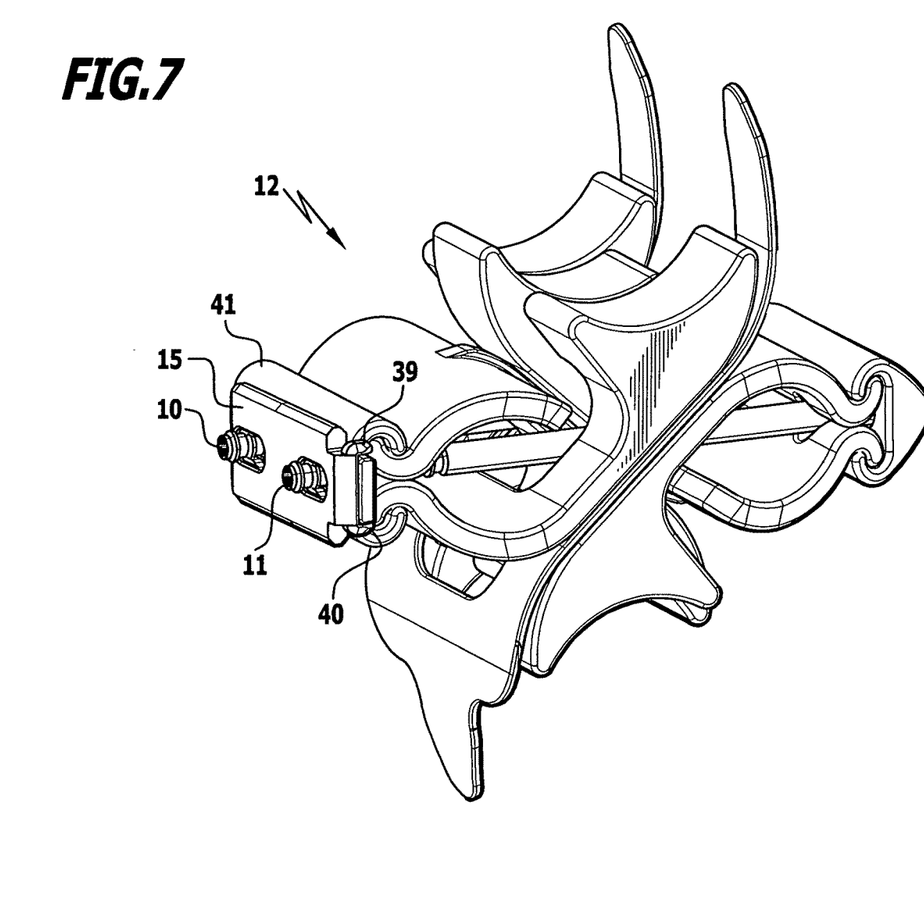
FIG. 7 shows a view similar to FIG. 6 after the severing of implant parts and after the bending of locking elements.

From the illustration in FIG. 5 it will be clear that there are arranged in the recesses 16, 17, which are immediately adjacent to the cutting edges 8, 9 of the cutting jaws 2, 3, deforming projections 37, 38, which project into the receiving space formed by the recesses 16, 17, and which, upon closing the cutting jaws 2, 3, bend over locking projections 39, 40 on the end plate 15. FIG. 6 shows these locking projections 39, 40 in the undeformed state on one side of the end plate 15, where they protrude in the plane of the end plate 15 towards opposite sides, whereas FIG. 7 shows how these locking projections 39, 40 are bent at right angles after the cutting procedure and thus lie with their side against a component 41 of the intervertebral implant 12 and thereby lock it against displacement. The locking projections 39, 40 are bent over by being made to abut on the deforming projections 37, 38 in the recesses 16, 17 during closure of the cutting jaws 2, 3, so that the cutting jaws assume a double function in this respect, namely firstly the deformation of the locking projections 39 and 40, and, secondly, the severing of the pins 10, 11.

The invention claimed is:

1. Surgical severing instrument, comprising:
    two cutting jaws movable from an open position to a cutting position by means of hand grips movable relative to each other,
    two clamping jaws movable relative to each other from an initial position to a clamping position arranged alongside the cutting jaws, and
    actuators, which, upon movement of the cutting jaws from the open position to the cutting position, simultaneously move the clamping jaws from their initial position to the clamping position,
    wherein:
        the cutting jaws are designed and adapted to sever components of a surgical implant;
        the components to be severed carry locking elements;
        the cutting jaws carry deforming projections designed to directly contact the locking elements of the components to be severed;
        during severing of the components by the cutting jaws, the deforming projections bend the locking elements and thereby lock the locking elements relative to other components or elements of the surgical implant.

2. Surgical severing instrument in accordance with claim 1, wherein at least one of the cutting jaws and the clamping jaws are movable relative to each other by being pivoted about a pivot axis.

3. Surgical severing instrument in accordance with claim 1, wherein the clamping jaws are each connected to an actuating lever, and the clamping jaws are moved from the initial position to the clamping position by the actuating levers being brought closer together.

4. Surgical severing instrument in accordance with claim 3, wherein the actuators are arranged on the hand grips of the severing instrument and engage the actuating levers of the clamping jaws.

5. Surgical severing instrument in accordance with claim 4, wherein the actuators are projections on the hand grips, which abut on outer sides of the actuating levers.

6. Surgical severing instrument in accordance with claim 4, wherein at least one of the clamping jaws and the actuating levers are constructed as a structural unit which is detachably connectable to the severing instrument.

7. Surgical severing instrument in accordance with claim 1, wherein a spring element which attempts to move the cutting jaws or the clamping jaws to their open position or initial position engages at least one of the cutting jaws and the clamping jaws.

8. Surgical severing instrument in accordance with claim 1, wherein a locking device for enabling movement of the clamping jaws from the initial position to the clamping position, but not in a reverse direction, is associated with the clamping jaws.

9. Surgical severing instrument in accordance with claim 8, wherein:
    the clamping jaws are each connected to an actuating lever,
    the clamping jaws are moved from the initial position to the clamping position by the actuating levers being brought closer together, and
    the locking device is constructed as a latching bar which is operative between the actuating levers of the clamping jaws.

10. Surgical severing instrument in accordance with claim 8, wherein the locking device is formed by latching surfaces on the clamping jaws, which latching surfaces are arranged concentrically with a pivot axis of the clamping jaws and abut on each other.

11. Surgical severing instrument in accordance with claim 1, wherein at least one of the clamping jaws and actuating levers connected to the clamping jaws are constructed as a structural unit which is detachably connectable to the severing instrument.

12. Surgical severing instrument in accordance with claim 11, wherein the structural unit is in the form of pliers having two arms pivotably connected to each other, which form the actuating levers and carry the clamping jaws at their distal ends.

13. Surgical severing instrument in accordance with claim 6, wherein the structural unit is in the form of pliers having two arms pivotably connected to each other, which form the actuating levers and carry the clamping jaws at their distal ends.

* * * * *